United States Patent [19]

Maillard et al.

[11] Patent Number: 4,541,856

[45] Date of Patent: Sep. 17, 1985

[54] PROCESS AND DEVICE FOR THE ANALYSIS OF THE HETEROGENEOUS FEATURES IN A TRANSPARENT MATERIAL

[75] Inventors: Alain Maillard, Soisy Sous Montmorency; Michel Pichon, Eaubonne, both of France

[73] Assignee: Isover Saint-Gobain, Courbevoie, France

[21] Appl. No.: 554,957

[22] Filed: Nov. 25, 1983

[30] Foreign Application Priority Data

Nov. 25, 1982 [FR] France .................................. 82 19753

[51] Int. Cl.⁴ .................................................. C03B 17/00
[52] U.S. Cl. .......................................... 65/29; 65/2; 65/11.1; 65/158; 65/164
[58] Field of Search ....................... 65/29, 2, 11.1, 158, 65/164

[56] References Cited

U.S. PATENT DOCUMENTS

| | | | |
|---|---|---|---|
| 3,814,946 | 6/1974 | Takahashi et al. | 250/572 |
| 4,021,217 | 5/1977 | Bondybey et al. | 65/29 X |
| 4,136,961 | 1/1979 | Young | 356/239 |
| 4,280,827 | 7/1981 | Murphy et al. | 65/29 X |

*Primary Examiner*—Arthur Kellogg
*Attorney, Agent, or Firm*—Oblon, Fisher, Spivak, McClelland & Maier

[57] ABSTRACT

The invention relates to the analysis of defects in materials such as molten glass. According to the invention, the material passes by a monochrome beam the wavelength of which is below $3 \times 10^{-6}$ m. The radiation is diffused by any defects present in the material. The analysis of the defects is conducted dependent on the position of the receiver detecting the diffused rays and on the shape of the signal received. The invention permits a continuous analysis of a flow of glass supplying a fiber-making machine.

20 Claims, 9 Drawing Figures

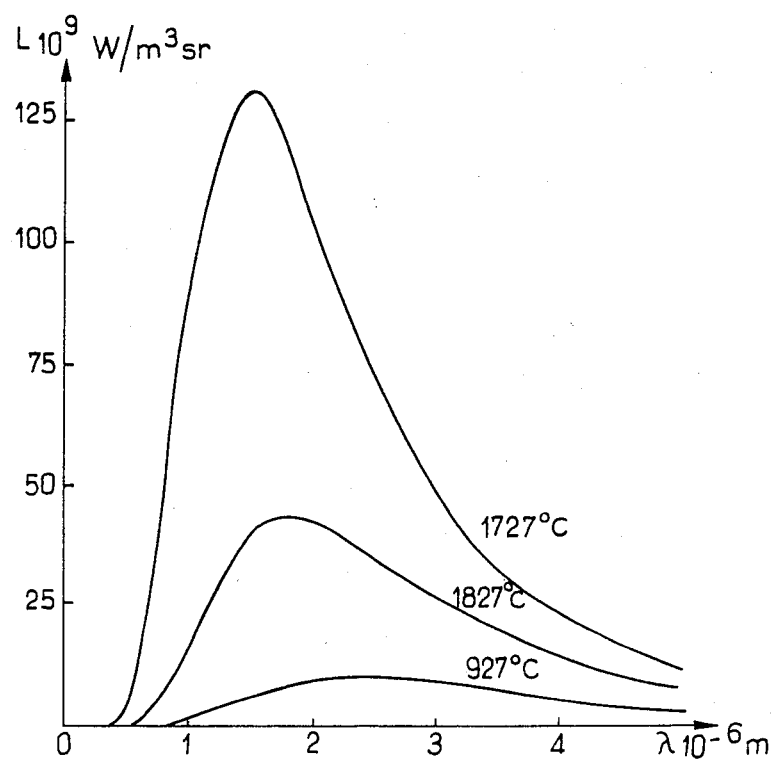
FIG_1
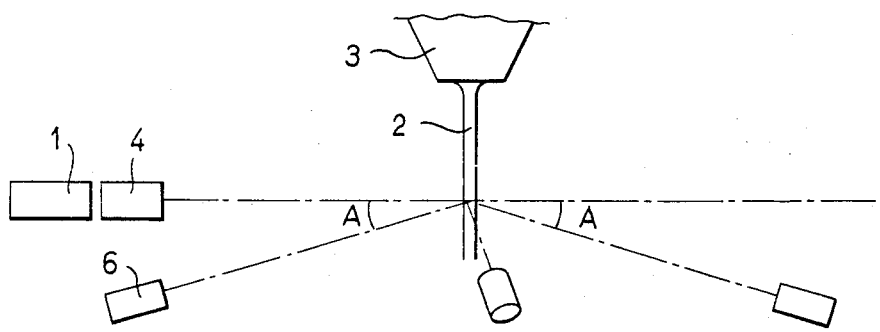
FIG_2

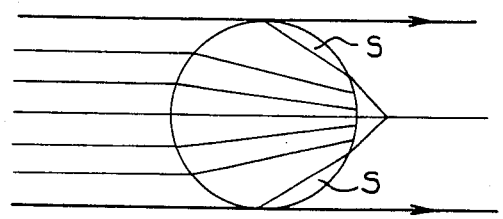
FIG_3
FIG_4a  FIG_4b
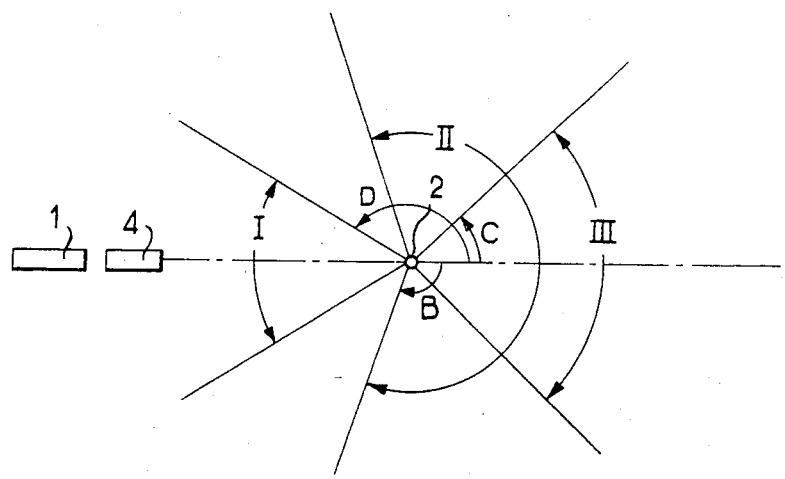
FIG_5

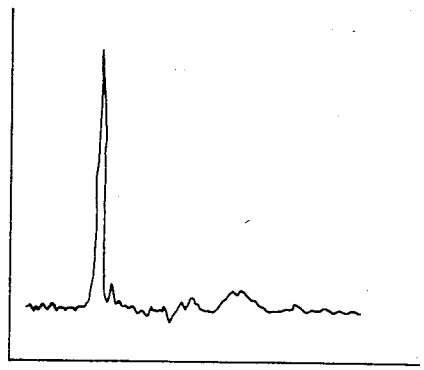
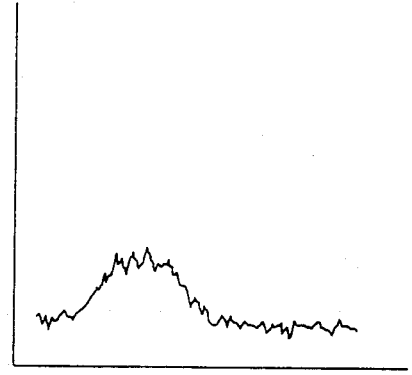
FIG_6a   FIG_6b
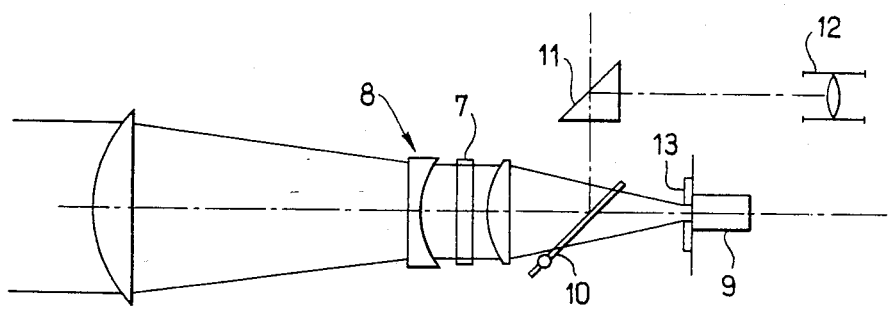
FIG_7

PROCESS AND DEVICE FOR THE ANALYSIS OF THE HETEROGENEOUS FEATURES IN A TRANSPARENT MATERIAL

BACKGROUND OF THE INVENTION

1. Field of the Invention

The invention relates to a process and a device for the analysis of heterogeneous features present in a transparent material. More particularly, the invention relates to the analysis of a material such as a glass material when the latter is in a molten state. The following descriprion is given witn reference to such materials having mass defects leading to a diffusion phenomena when they are subjected to appropriate radiation.

2. Description of the Prior Art

More generally, in production methods using a glass material in the molten state, the supply of glass material is continuous whether there is involved for example the supplying for fiber-making methods or operations leading to the formation of glass sheets and in which the material is cast in sheets, etc.

It is important to be able to follow the evolution of homogeneity defects in the material, particularly so as to determine their influence upon the quality of the products produced. Furthermore, the knowledge of the influence of defects upon quality may possibly permit, through a modification of the factors which are the cause of these defects, improving the quality of the products obtained.

To this end, it is necessary not only to detect the presence of the defects, but also to determine their nature, their size and number and to follow their evolution over time, etc.

SUMMARY OF THE INVENTION

The invention has as its object providing means suitable for the study of these defects in such environments.

The study of homogeneity defects in materials such as molten glass is difficult for several reasons. A first difficulty originates from the fact that the material must be analyzed in most cases at the very moment when it is treated in molds. Analysis must then be instantaneous and it must not disturb the supplying of materials to the treating installations.

Other difficulties are associated with the conditions of temperature and the conditions of access imposed by the manufacturing station. The means used for measurement in any analysis must remain reliable in such an environment. In the case of optical measurements, the radiation emanating from the molten material constitues a substantial hindrance.

The analysis of glassmaking materials is also complicated by the fact that defects are, by their nature, their size and their abundance, very diverse.

The defect found in any mass of glassmaking materials are traditionally classified in three categories: bubbles, "blisters" and solid or non-molten matter.

The non-molten matter, as the name indicates, consists of solid particles entrained by the molten material. They originate mainly from the raw materials used, or fragments of refractory materials wrenched off the walls of the melt furnaces. For the analysis according to the invention which brings into play optical devices as described hereinbelow, the non-molten materials are characterized by an irregular surface structure and their opacity.

By "blisters" it is intended to denote all the inclusions which, though transparent, are distinguishable from the mass of the glass. They are, in particular, particles of raw materials insufficiently "digested" by the adjacent molten mass. Due to their characteristics, blisters are classified between glass and the non-molten material. In particular, although transparent, their refraction index is different from that of the surrounding glass mass.

In glassmaking, bubbles are always present, though in very variable porportions depending on the method of melting and refining used. In the making of glass sheets, refining is relatively extensive and bubbles are very scarce. On the other hand, for the making of fibers intended for insulation, the presence of bubbles is often regarded as less of a drawback. In this case, refining, when present, is much more abbreviated and bubbles are very plentiful and in a great diversity of sizes.

The analysis according to the invention is carried out by taking advantage of the differences of characteristics of the glassmaking material, on the one hand, and defects, on the other hand, when the material is exposed to an electromagnetic beam, the wavelength of which is smaller than the average dimension of these defects.

The analysis according to the invention also takes advantage of the fact that the various types of inclusions have different effects as regards such a beam.

Generally speaking, the method of analysis according to the invention comprises the formation of a monochrome beam, directed at the material to be analyzed, and the detection and the analysis of the radiation diffused by the defects of the material.

As it passes through the transparent medium the beam encounters the various types of defects described above. By diffraction, refraction or reflection of a fraction of the incident beam there comes about that which we describe generally as "diffusion". This diffusion has features (direction, intensity) which are characteristics of the defects met with, which permits distinguishing amongst them.

For this type of analysis with optical means, it is necessary to take into account the fact that glassmaking materials in the molten state have a very high radiation emission of their own which covers an extensive range of wavelengths in the manner of a black body.

The radiation emitted by the glass constitutes a very substantial "background noise" which may hide the diffusion phenomena used in the invention. For a good separation of the useful radiation, one chooses according to the invention a monochrome emitter source, the frequency of which is situated in a range of low emissivity for the molten glass. By associating this emitter source with a receiver fitted with a filter centered on the same frequency, it is possible to minimize the interference resulting from radiation foreign to the analysis.

As described earlier, the wavelengths of the incident beam must be selected depending upon the transparency of the material studied, and the range of emissions of the material, particularly when the latter is brought to a high temperature; it must also be dependent upon the dimensions of the defects it is desired to detect. For diffusion phenomena to be clearly manifested, under conditions which will be made clearer hereafter, it is preferable that the wavelength should not be greater than one-twentieth of the dimension of the defects intended to be detected.

In the case of defects detected in molten glass under usual production conditions, it is advantageous to select a wavelength which is not greater than $3 \times 10^{-6}$ m.

Preferably, the wavelength is between 0.4 and $2 \times 10^{-6}$ m.

As is described further on, with account being taken of the characteristics of the emission curves of glassmaking materials, the wavelengths utilized are advantageously shorter than half the wavelengths corresponding to the emission maximum for temperatures ranging from 500° to 2000° C.

Studies conducted also show that the form of the diffused signals are dependent upon the geometry of the incident beam. Experimentally, it is indeed observed that in order to have well defined signals characteristic of the defects observed, it is preferable to use a very fine incident beam.

Several factors suggest that it is preferable to have a fine beam. Generally speaking, it may be considered that the finer the beam, the better the resolving power of the system. For the present invention, this results in a better individualization of the defects observed. This may be explained by the fact that by reducing the thickness of the beam one limits the risks of superimposition of signals corresponding to several defects which would occur simultaneously. Furthermore, the shape of the signals recorded is more characteristic of the defects as the beam is made finer.

Considerations of a technical nature require that in practice the reduction of the thickness of the beam is limited. For the analyses carried out on glassmaking materials, and in particular to study the bubbles they contain, these practical limits usually cause no hindrance. The fineness that can be achieved is sufficient to detect the bubbles which, because of their size, may have an influence on the properties of the final product.

In the case of the analysis of a stream of molten glass, the analysis beam is preferably plane and cuts the thread along a straight section. Preferably, the thickness of the beam is at most equal to the dimension of the smallest defects to be detected. For a glass stream serving, for example, for the supply of a fiber-making machine, the beam should not exhibit, at the level of the glass stream, a thickness greater than 0.2 mm, and, advantageously, not greater than 0.1 mm.

Independently of the diffusion phenomena due to defects, the incident beam gives rise to reflection and refraction phenomena on the surface of the glass stream analyzed. The radiation directly transmitted through the stream or reflected on its surface is normally very intensive when compared to that diffused by the defects. To be able to detect the latter correctly, it is necessary to locate the receiver outside the path of this radiation transmitted or reflected on the surface of the stream.

In the description which follows, the analysis is restricted to that of a stream of molten glass flowing continuously and permanently exhibiting a circular straight section of practically constant dimension and position. This type of glass stream is commonly found, for example, in feeding devices for centrifugal fiber-making machines. On these machines, the system according to the invention is particularly useful. Although the material is at a very high temperature and gives rise to intense emissions, the analysis according to the invention permits following up continuously the evolution of the defects without altering machine operation. Similar arrangements are applicable when the analyzed material exhibits a different geometry, particularly a plane form.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts through the several views and wherein:

FIG. 1 shows a set of emission curves of a glassmaking material, showing the wavelength pattern for different temperatures;

FIG. 2 is a diagram illustrating a method of analysis according to the invention;

FIG. 3 shows a straight section of a glass stream illustrating the areas subjected to the radiation emitted by the monochrome source;

FIG. 4a schematically shows the effect of a solid inclusion in relation to the monochrome radiation;

FIG. 4b schematically shows the effect of a bubble on the monochrome radiation;

FIG. 5 shows preferred positions for the setting up of a detector or detectors used for the method of analysis represented in FIG. 2 in a plane containing the transmitter and perpendicular to the glass thread.

FIG. 6a and 6b show the form of signals typically collected according to the invention; and FIG. 7 schematically shows a receiving device.

DETAILED DESCRIPTION OF THE PREFERRED EMBODIMENTS

The curves of FIG. 1 show in simplified manner the general pattern of the intensity of emissions for glass heated to 927°, 1327° and 1727° C. For these three curves there is observed the presence of a very pronounced emission intensity maximum with a very rapid increase in intensity on the side of smaller wavelengths, and a relatively slow decrease in emission intensity on the side of the larger wave lengths. These peculiarities are more pronounced as the temperature is higher.

It is thus observed that the emission intensity for wavelengths below half the wavelength associated with the maximum intensity is only a few hundredths, or less, of the emission intensity in the maximum emission zone. Operating as we have indicated, with a source whose wavelength is below said half wavelength of the emission maximum, the emissions of the material remains sufficiently low so as not to hinder analysis.

As a whole, the arrangement for the carrying out the method of the invention comprises (FIG. 2) a generator 1 of a coherent energy beam which transmits energy in the direction of a stream of material 2 flowing from the orifice of a nozzle 3. The stream 2 has a substantially circular straight section.

An optical system 4 modifies the beam in such a way that at the position where said beam cuts the path of the stream 2, it presents itself in a practically plane form. In other words, the beam irradiates only a small fraction of the length of the stream of material. Preferably, the plane of the beam is selected to be substantially perpendicular to the direction of flow of stream 2.

A different angle is also possible if the local overall size conditions justify it. However, from the point of view of the analysis method, a different angle does not supply advantages. If the beam used is not at right angles to the stream, the optimum positions for the receiver described below must be modified accordingly. The modifications introduced in this hypothesis are those which follow systematically from known optical laws.

The emitted coherent beam, or laser beam, has normally a circular section. Its transformation into a plane beam is obtained, for example, with the aid of a known optical system such as a cylindrical lens.

When the initial beam is of small size in relation to the diameter of the glass stream 2 studied, it passes first through an enlarger in such a way that the plane beam originating from the cylindrical lens extends throughout the height of the stream.

A receiver 6, sensitive to the radiation diffused in the stream 2, is oriented in the direction of the area of intersection of the stream by the beam.

When the frequency of the radiation emitted by the generator is suitably selected, the power of this radiation may be relatively low but should be sufficiently high that the signals received by the receiver have an amplitude sufficient to distinguish them without difficulty from the "background noise" constituted by the radiation.

To permit satisfactory analysis, the various elements used should meet a series of well specified conditions. These conditions relate in particular to relative arrangements of the transmitter, the receiver and the stream analyzed.

The method of propagation of the beam in the stream of material permits a clear understanding of how best to set out the elements of the arrangement.

The beam, when it encounters the glass stream, is reflected and/or refracted according to the point of incidence on the periphery of the stream. Taking into account the fact that the beam is directed along a straight section of the glass stream the radiation transmitted or reflected is situated in the same plane as the beam and at right angles to the glass stream. To prevent the saturation of the receiver by these radiations which could mask the diffusion originating from the defects analyzed, it is therefore necessary to place the receiver outside the plane in question.

A low level of radiation originates also from multiple reflections on the internal faces of the stream analyzed. These multiple reflections, however, become very rapidly attenuated. A small angle relative to the plane of incidence is ordinarily sufficient for this stray radiation not to be detected. Accordingly, the angle of sight of the receiver in relation to the plane of the incident beam A remains preferably relatively low. Advantageously, this angle is not below 5° and is not greater than 20°. A smaller angle could lead to the reception of the radiation originating from multiple reflections in the stream. If, however, the angle is too greater, the additional reduction of the intensity of the radiation originating from the stream is very small, whereas the reduction of the radiation coming from the defects is very substantial. It is therefore preferable to remain within the limits indicated above which correspond to values of the ratio of a useful signal constituted by the radiation originating from the defects to that which may be described as a background noise and which includes the residual radiation reflected or refracted on the surface of the glass stream in the direction of the receiver.

In FIG. 3 there is represented in cross-section the path of the radiation in the stream. Due to refraction inside the stream, it is noticed that two areas S of the stream section are not passed through by the radiation. It is evident that only those defects which, in the section of the stream are situated on the path of the radiation, can give rise to detectable signals. The quantitative results of the analysis must take into account the fact that a constant fraction of the stream escapes notice.

Nevertheless, it is preferable to restrict the extrapolation of the results beyond that which is actually analyzed, and therefore it is desirable that the fraction of section of stream actually scanned by the beam be as wide as possible. This implies, obviously, that the incident beam should be at least as wide (as high in FIG. 3) as the glass stream.

FIG. 4a shows very schematically the phenomenon that is observed when the beam reaches solid particles. Diffusion is then effected essentially by reflection. Account being taken of the surface irregularities of these particles, diffusion takes place in multiple directions, this being represented in the figure by arrows. Quite obviously, diffusion is not restricted to the plane of the figure. Moreover, without entering into a theoretical study, it will be understood that a maximum of reflection develops in a direction opposite that of the incident light. In other words, the most favorable position for detecting the signals corresponding to the presence of solid particles is in the vicinity of the transmitter.

It is described above how the receiver is placed relative to the plane of the incident beam. It is therefore necessary to add to these conditions the further condition that the optical axis of the transmitter and the optical axis of the receiver form between them an angle D, as projected on the plane of the incident beam (FIG. 5) which is not less than 150° C. on either side of the axis of the transmitter, when seen projected on the plane of the incident beam. This is shown in FIG. 5 which clarifies, in projection in the plane of a beam perpendicular to the stream, the zones in which the detection of each type of defect is most favorable. For solid particles this zone is I.

The considerations given in relation to the defects constituted by solid particles may also be drawn as regards bubbles or blisters.

FIG. 4b shows the path of the rays meeting a bubble. The beam goes through the bubble, but its orientation is substantially modified. If part of the radiation is found in an overall direction differing little from the initial direction, the behaviour of the optical system which is constituted by the bubble itself and by the glass stream, brings about the phenomenon that the diffused radiation is greatly scattered. It accordingly covers a substantial portion of the surrounding space, with the exception of the areas situated near the transmitter.

In FIG. 5, which is the plane of the incident beam, the effective area for the light diffused by the bubbles is indicated at II. In relation to the plane of symmetry of the system defined by the glass stream and the transmitter, the limit zone of diffusion usable to analyze bubbles is defined by planes forming with the plane of symmetry an angle B which is at most equal to about 100° and preferably at most equal to 110°.

The comparison of the preferred positions of the receiver for the observation of the solid particles on the one hand, and the bubbles on the other hand, shows that these positions are quite separate. The separate observation of these two types of defects does not, therefore, present any difficulties.

The behavior of light encountering blisters is close to that of light encountering bubbles. In particular, blisters are transparent. Their influence upon radiation is, however, less definitely marked than that of bubbles, perhaps because they have a refraction index close to that of glass and because they do not have a well defined form. The transition from the glass mass to the blister is effected by a progressive modification of the medium and of its properties, particularly its optical properties. There is observed, again without going into technical considerations, that under these conditions the diffusion of the usefully detectable radiation is restricted to a space near the path followed by the radiation which is not affected by defects in the glass stream.

Experimentally, with reference to the plane of symmetry of the whole, the zone in which a useful diffusion due to blisters can be observed is limited by planes forming with the plane of symmetry an angle C of at most 50° and preferably equal at most to 40°. In FIG. 3 this corresponds to Zone III.

By comparing that which has been mentioned about the zones in which the bubbles and blisters can be observed, it will be noticed that these zones overlap only in part. It is therefore possible in practice to detect bubbles alone in the area corresponding to an angle of 50° to 110°. On the contrary, in the zone of angles below 50°, one detects simultaneously the rays diffused by the bubbles and by the blisters.

There is described above, in a general manner, how to site the receiver to detect the signals associated with the presence of defects. It is also possible to anticipate what kind of a structure these signals have. The theoretical study of the propagation phenomena, as mentioned above, is relatively complex and does not supply more precise elements than do experimental results. The latter reveal two very distinct structures according as to whether one considers the bubbles or the solid particles.

The general appearance of the intensity of the signal received, as a function of time, shows when one operates under the conditions of emission and reception indicated hereinabove, a very pronounced and very narrow peak for bubbles (FIG. 6a), and (FIG. 6b) a much more spread out shape with a less pronounced maximum for solid particles.

Without going into theoretical considerations, an intuitive appreciation of the phenomenon makes it possible to understand this difference. The radiation originating from the solid particles is much more irregular for the reason that it is reflected and/or refracted on a surface which is itself irregular, while bubbles exhibit a more definite geometry with, relative to the adjoining medium, a sudden variation of the refraction index. These interpretations, however incomplete they may be, correspond with the actual observations.

Blisters produce a signal of the same type as do solid particles. For this reason, even if the presence of the signals corresponding to the blisters cannor be dissociated from that of the bubble signals, the identification of one from the other remains nevertheless possible. As regards the distinction between insoluble matter and blisters, it results from the position of the receiver. As noted above, the fields of observation of solids and blisters are entirely distinct.

The signals obtained can also serve for the study of the dimensions of the defects detected.

The measuring of a single signal does not permit one to accurately determine the size of the particle from which it emanates. It is obvious that, generally speaking, the signal is all the more substantial as the size of the defect is greater. However, account must be taken in this appraisal of the position of the defect in the stream. This position determines both the intensity of the incident radiation received on the defect and the intensity diffused in the direction chosen for reception. Moreover, glass at the temperatures considered is very absorbent for a wide range of frequencies. Depending on the position of the defect and, consequently, on the distance covered in the stream material, the absorption is more or less substantial. The influence of the position of the defect in the glass stream upon the intensity of the signal is thus considerable.

Over a great number of defects however, the distribution of sizes remaining the same, the measuring of the overall intensity of the signal permits a statistical determination of the size of the defects detected.

In any event, the defects detected constitute only a fraction of the defects actually present since certain areas of the stream are not observed as the radiation does not go through them. Added to this, the small size of the surface of the receiver relative to the overall space into which the radiation emitted by the defects may be directed, means that that only part of this radiation is detected. Under these conditions measurements may lead only to a statistical value.

Thus, under the conditions of operation corresponding to the example described hereinbelow, comparative measurements taken by collecting samples which are studied outside the installation have shown that the proportion of defects detected by the method according to the invention is of the order of 10 to 20%. The known percentage under specific conditions is fairly strictly known. With the maximum observed error of the order of 1%, an error quite admissible under the operational conditions and for the results sought, the method may be regarded as reliable, account being taken of the fact that it is not a question of checking a material to make sure of the absence of any defect, but of a statistical measurement for defects which appear with a relatively appreciable frequency.

For the sake of example, a study was conducted to analyze the molten glass stream flowing in a centrifugal fiber-making machine of the type described particularly in French Pat. No. FR-A-2 443 436.

The analyzing device includes the various elements which are shown on FIG. 2, i.e. a transmitter 1 and a receiver 6 with which are associated means for the processing of the signals received.

In the case under study, the light source is constituted by a laser which produces radiation which is quite definitely monochrome with a strong luminance even for low powers. The laser used, chosen for its low cost, is of the He-Ne type ($\lambda = 632.8 \times 10^9$ m), of 5 mW power.

The laser produces a cylindrical beam 1 mm in diameter. This beam is treated optically, by means of a magnifier and a cylindrical lens, to give it a plane form of very small thickness (less than 0.08 mm). This beam is expanded and focused onto the glass stream which it intersects along a straight section throughout its width which is of the order of one centimeter.

The assembly of the transmitter and of the associated optics is sited in a cooled casing to protect it against the heat released by the fiber-making machine. The optical axis of the system is disposed horizontally and in such a way as to intersect the glass stream. The distance between the transmitter and the stream, determined by the focal distance of the cylindrical lens, is one meter.

Account being taken of the conditions particularly of temperature and overall size, in the immediate vicinity of the glass stream, it is important according to the invention to be able to site the transmitter device, and the receiver, at some distance from the stream, even if in the case of the receiver this results in a decrease of the power of the signals received.

The receiver (FIG. 7) comprises a filter 7 of the interference type with a low pass band ($\delta\lambda = 3.10^{-9}$ m) centered on the wavelength of the transmitter. This filter permits eliminating the greater part of the stray radiation emitted by the incandescent stream.

The optics 8 associated with this interference filter forms the image of the part of the stream touched by the beam on a diaphragmed photodiode 9. The photodiode used, of PIN type, operates on photo-voltaic, a low noise pre-amplifier being associated with the photodiode.

The assembly of the cell filter and of the preamplifier is disposed in a cooled casing sited 0.75 m away from the glass stream. It is outside the plane of direct propagation of the light beam.

The angle A of the sighting axis of the receiver relative to the plane of the incident beam is 10°.

In practical terms it seems preferable to place the receiver in the plane of symmetry of the optical assembly. The 180° and 0° positions indeed correspond to a maximum of intensity for the rays respectively reflected and refracted. Moreover, these positions are those for which the probability of the presence of the diffused rays is the highest for defects which are necessarily distributed haphazardly throughout the section of the glass stream.

The optical system of the receiver used is schematically represented in FIG. 7. It comprises, in addition to the elements previously listed, a sighting assembly formed by a pivoting mirror 10, a reflecting prism 11 and an eye-piece 12. With the aid of this sighting assembly, the image of the part of the stream illuminated by the laser, and formed through the optical system of the receiver, is placed in coincidence with the slit of the diaphragm 13 situated in front of the cell.

The electric signal emitted by the pre-amplifier then passes into an assembly (not shown) for processing the signal.

Typically, the signal is cleared of the high frequency noise originating essentially from the external circuits and strays by a low-pass filter of 10 kHz frequency. The filtered signal is amplified and directed onto filters permitting taking into account only significant signals. Pulse counters with adjustable thresholds permit the counting of the defects and possibly their classification to to form a histogram of such defects. It is also possible by this processing to distinguish bubbles from blisters for the receiver sited at 180° from the transmitter.

In the case under study, the device comprises only one receiver placed successively in the three positions previously indicated. It is evident that a similar device may be made up having two or three receivers operating simultaneously and each placed in one of these positions.

By means of the device previously described, the systematic study of the glass stream has permitted, in the case under consideration, the identification and the counting of bubbles. The measurements were taken after calibrating the results.

Analysis thus showed the presence in the glass under study of a very large quantity of bubbles (of the order of 1000 per kilo of glass) the sizes of which are greater than 0.01 mm and for the most substantial ones are of the order of one millimeter.

The blisters and non-molten material are of a much more restricted number, about 10 per kilo and they appear in an irregular manner particularly during a change of series of operation in the preparation of the material.

By taking samples during operation, and analyzing them when cooled, it has been possible to observe satisfactory concordance with the measurements taken on molten material according to the invention. The proportion of defects detected remains constant for various frequencies of appearance. The variation in the ratio of measurements does not exceed 1%.

In the system in FIG. 2, calibration is associated not only with a precise geometrical arrangement but also with the diameter of the glass stream for optical reasons, and especially by virtue of the substantial absorption of glass at the temperatures considered. By associating a measuring device with the diameter of the stream (for example a system of aligned photodiodes), it is possible to weigh the signals received automatically so that the calibration may be independent of the diameter of the stream.

Obviously, numerous modification and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method of analyzing a stream of molten glass to detect the frequency of translucent bubbles of gas, blisters of non-homogeneous translucent material, and opaque solid particles entrained in the stream of molten glass, said method comprising the steps of:
   (a) directing as essentially planar beam of monochromatic light having a wavelength no greater than $3 \times 10^{-6}$ m through the stream of molten glass in a light transmission direction from a first side of the stream of molten glass to a second side of the stream of molten glass, whereby said essentially planar beam of monochromatic light is diffused in identifiably different fashions by translucent bubbles of gas, blisters of non-homogeneous translucent material, and solid opaque particles entrained in the stream of molten glass;
   (b) detecting the frequency of opaque solid particles entrained in the stream of molten glass by detecting light reflected from the opaque solid particles into a first receiver located on the first side of the stream of molten glass and having an optical axis which is positioned out of the plane of said essentially planar beam of monochromatic light by an angle of between 5° and 20° and which is positioned at an angle D to the optical axis of the transmitter of not less than 150° measured with respect to the light transmission direction of said essentially planar beam of monochromatic light;
   (c) detecting the frequency of translucent bubbles of gas in the stream of molten glass by detecting light which passes through the translucent bubbles of gas but the direction of which is modified by the bubbles, the light passing through the bubbles being detected by a second receiver located on the second side of the stream of molten glass and having an optical axis which is positioned out of the plane of said essentially planar beam of monochromatic light by an angle of between 5° and 20° and which is positioned at an angle B of at most 110° measured with respect to the light transmission direction of said essentially planar beam of monochromatic light; and (d) detecting the frequency of blisters of non-homogeneous translucent material in the stream of molten glass by detecting light which passes through the blisters of non-homogeneous translucent material but the direction of which is modified by the blisters, the light the light passing through the blisters being detected by a third receiver located on the second side of the stream of molten glass and having an optical axis which is positioned out of the plane of said essentially planar beam of monochromatic light by an angle of between 5° and 20° and which is positioned at an angle C of at most 50° measured with respect to the light transmission direction of said essentially planar beam of monochromatic light.

2. A method as recited in claim 1 wherein the plane of said essentially planar beam of monochromatic light is at least substantially perpendicular to the direction of flow of the stream of molten glass.

3. A method as recited in claim 1 wherein the thickness of said essentially planar beam of monochromatic light is not greater than 0.2 mm.

4. A method as recited in claim 3 wherein the thickness of said essentially planar beam of monochromatic light is not greater than 0.1 mm.

5. A method as recited in claim 1 wherein the wavelength of said beam of monochromatic light is between 0.4 and $2 \times 10^{-6}$ m.

6. A method as recited in claim 1 wherein said essentially planar beam of monochromatic light is at least as wide as the stream of molten glass and the entire width of the stream of molten glass passes through said essentially planar beam of monochromatic light.

7. A method as recited in claim 1 wherein the angle B is at most equal to 100°.

8. A method as recited in claim 1 wherein the angle C is at most equal to 40°.

9. A method as recited in claim 1 wherein the frequency of the translucent bubbles of gas and the frequency of the blisters of non-homogeneous translucent material are detected by the same receiver.

10. A method as recited in claim 1 wherein the frequency of the translucent bubbles of gas and the frequency of the blisters of non-homogeneous translucent material are detected by different receivers.

11. Apparatus for analyzing a stream of molten glass to detect the frequency of translucent bubbles of gas, blisters of non-homogeneous translucent material, and opaque solid particles entrained in the stream of molten glass, said apparatus comprising:

(a) a source of an essentially planar beam of monochromatic light having a wavelength no greater than $3 \times 10^{-6}$ m, said source having an optical axis and being positioned so that, during use of the apparatus, the essentially planar beam of monochromatic light is passed through the stream of molten glass in a light transmission direction from a first side of the stream of molten glass to a second side of the stream of molten glass, whereby the essentially planar beam of monochromatic light is diffused in identifiably different fashions by translucent bubbles of gas, blisters of non-homogeneous translucent material, and opaque solid particles entrained in the stream of molten glass;

(b) a first receiver means located on the first side of the stream of molten glass for detecting the frequency of opaque solid particles entrained in the stream of molten glass by detecting light reflected from the opaque solid particles into said first receiver means, said first receiver means having an optical axis which is positioned out of the plane of said essentially planar beam of monochromatic light by an angle of between 5° and 20° and which is positioned at an angle D to the optical axis of the source of not less than 150° measured with respect to the light transmission direction of said essentially planar beam of monochromatic light;

(c) a second receiver means for detecting the frequency of translucent bubbles of gas in the stream of molten glass by detecting light which passes through the translucent bubbles of gas but the direction of which is modified by the bubbles, said second receiver means having an optical axis which is positioned out of the plane of the essentially planar beam of monochromatic light by an angle of between 5° and 20° and which is positioned at an angle B of at most 110° to the optical axis of said source measured with respect to the light transmission direction of said essentially planar beam of monochromatic light; and (d) a third receiver means for detecting the frequency of blisters of non-homogeneous translucent materials in the stream of molten glass by detecting light which passes through the blisters of non-homogeneous translucent materials but the direction of which is modified by the blisters, said third receiver means having an optical axis which is positioned out of the plane of the essentially planar beam of monochromatic light by an angle of between 5° and 20° and which is positioned at an angle C of at most 50° to the optical axis of said source measured with respect to the light transmission direction of said essentially planar beam of monochromatic light.

12. Apparatus as recited in claim 11 wherein said source is positioned so that, during use of the apparatus, the plane of the essentially planar beam of monochromatic light is at least substantially perpendicular to the direction of flow of the stream of molten glass.

13. Apparatus as recited in claim 11 wherein said source produces an essentially planar beam of monochromatic light which is not greater than 0.2 mm in thickness.

14. Apparatus as recited in claim 13 wherein said source produces an essentially planar beam of monochromatic light which is not greater than 0.1 mm in thickness.

15. Apparatus as recited in claim 11 wherein said source produces monochromatic light the wavelength of which is between 0.4 and $2 \times 10^{-6}$ m.

16. Apparatus as recited in claim 11 wherein:

(a) said source produces a beam of monochromatic light which is at least as wide as the stream of molten glass and (b) said source is positioned so that the entire width of the stream of molten glass passes through the essentially planar beam of monochromatic light.

17. Apparatus as recited in claim 11 wherein the angle B is at most equal to 100°.

18. Apparatus as recited in claim 11 wherein the angle C is at most equal to 40°.

19. Apparatus as recited in claim 11 wherein said second and third receiver means are the same receiver means.

20. Apparatus as recited in claim 11 wherein said second and third receiver means are different receiver means.

* * * * *